United States Patent [19]

Bay

[11] Patent Number: 4,774,360

[45] Date of Patent: Sep. 27, 1988

[54] CONVERTING ENOL ESTER PRECURSOR OF A BENZOYL-1,3-CYCLOALKYLDIONE TO A BENZOYL-1,3-CYCLOALKYLDIONE

[75] Inventor: Elliott Bay, Ridgefield, Conn.

[73] Assignee: Stauffer Chemical Company, Westport, Conn.

[21] Appl. No.: 67,045

[22] Filed: Jun. 29, 1987

[51] Int. Cl.⁴ .............................................. C07C 45/54
[52] U.S. Cl. ..................................... 568/306; 568/310
[58] Field of Search ................ 508/306, 319, 306, 310

[56] References Cited

U.S. PATENT DOCUMENTS 4,695,673 9/1987 Heather et al. ...................... 568/310

FOREIGN PATENT DOCUMENTS 0186118 12/1985 European Pat. Off. ............ 568/306

OTHER PUBLICATIONS

Duboudin et al., Synthesis, 1982, pp. 212–214.
Hertenstein et al., Chem. Ber., vol. 1;13, pp. 3783–3802 (1980).

Primary Examiner—James H. Reamer
Attorney, Agent, or Firm—Joel G. Ackerman; Richard P. Fennelly

[57] ABSTRACT

Enol ester precursors of benzoyl-1,3-cycloalkyldiones (e.g., the enol ester precursors of 2-(2'-nitrobenzoyl)-1,3-cyclohexanedione compounds) are converted to the desired benzoyl-1,3-cycloalkyldiones by heating the precursor in the presence of base and a catalytic amount of a trialkylsilylcyanohydrin as a cyanide source.

9 Claims, No Drawings

CONVERTING ENOL ESTER PRECURSOR OF A BENZOYL-1,3-CYCLOALKYLDIONE TO A BENZOYL-1,3-CYCLOALKYLDIONE

BACKGROUND OF THE PRESENT INVENTION

Published European Patent Application No. 186,118 describes certain 2-(2'nitrobenzoyl)-1,3 cyclohexanedione compounds which have utility as herbicides. It indicates that, in preparing the desired benzoyl-1,3-cycloalkyldione end product, an enol ester precursor thereof is subjected to a rearrangement to the end product by use of a base in the presence of a "cyanide source" as catalyst. The types of cyanide sources enumerated are: alakali metal cyanides; cyanohydrins of methyl alkyl ketones; cyanohydrins of benzaldhyde or of $C_2$–$C_5$ aliphatic aldehydes; tri (lower alkyl) silyl cyanides; and hydrogen cyanide itself which is said to be inexpensive and to produce a rapid reaction. This published patent application is devoid of any suggestion of using a trialkylsilylcyanohydrin as a catalyst for such an enol ester rearrangement reaction.

Trialkylsilylcyanohydrins are a known class of compounds. Certain trimethylsilylcyanohydrins have been characterized in Synthesis, March 1982, pp. 212–214 as being useful as acyl anion equivalents in many synthetic transformations and as reagents for the synthesis of alpha, beta-unsaturated nitriles, beta-amino-alcohols, delta$^2$-butenolides, and alpha-hydroxyamides. To the best knowledge of the present inventor, trialkylsilylcyanohydrin compounds have not been shown or been suggested as being useful as a catalyst for the conversion procedure of the instant invention or one similar to it.

SUMMARY OF THE PRESENT INVENTION

The present invention relates to conversion of the enol ester precursor of a benzoyl-1,3-cycloalkyldione to the benzoyl-1,3-cycloalkyldione by heating the enol ester precursor in the presence of base and a catalytic amount of a trialkylsilylcyanohydrin to affect such conversion.

DETAILED DESCRIPTION OF THE PRESENT INVENTION

The enol ester precursor of the benzoyl-1,3-cycloalkyldione has the general formula:

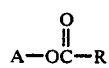

where R is a substituted or unsubstituted phenyl group and A is a substituted or unsubstituted hydrocarbyl ring with a C=O moiety forming the ring two carbons removed from the carbon linked to the single bonded benzoyl oxygen atom and a carbon-carbon double bond from the carbon linked to that benzoyl oxygen and the carbon of the ring between that carbon and the one forming the aforementioned C=O moiety of the ring. Particularly preferred compounds of this type are more fully described in the aforementioned published European Patent Application No. 186,118 and in its U.S. counterpart (U.S. Ser. No. 802,135, filed Nov. 29, 1985, which is incorporated herein by reference), which is a continuation-in-part of U.S. Ser. No. 683,900, filed Dec. 20, 1984. Such compounds are herbicides and are defined as 2-(2'-nitrobenzoyl)-1,3-cyclohexanediones.

The conversion of the aforementioned enol ester precursor of the benzoyl-1,3-cycloalkyldione yields the desired benzoyl-1,3-cycloalkyldione which has the formula:

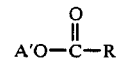

where R is as defined before and A' is a 1,3-cycloalkyldione having two C=O moieties as part of its ring structure, each flanking each side of the ring carbon bonded to the single bonded benzoyl oxygen atom. The cycloalkyl group is preferably cyclohexyl.

Some representative benzoyl-1,3-cycloalkyldione end products include 2-(2'-nitrobenzoyl)-5,5-dimethyl-1,3-cyclohexanedione, 2-(2'-nitro-4'-trifluoromethylbenzoyl)-1,3-cyclohexanedione, and 2-(2'-nitrobenzoyl)-1,3-cyclohexanedione.

The conversion of the enol precursor described before to the desired end product is achieved by reacting one mole of the enol ester precursor with about one to about four moles (preferably 2 moles) of base and about 0.01 mole to about 0.5 mole or higher of trialkylsilylcyanohydrin as a cyanide source). The mixture can be stirred until the conversion (or arrangement) reaction is substantially complete at a temperature of below about 50° C., preferably 20°–40° C. and the desired product is recovered by conventional means.

Representative trialkylsilylcyanohydrin compounds include those of the formula:

where R and R' can be the same or different with R being alkyl, cycloalkyl or phenyl and R' being alkyl. A representative compound of this type is 2-cyano-2-(trimethylsilyloxy)propane.

The types of base which can be used are preferably "moderate bases", i.e., those whose strength or activity lies between that of the strong bases (such as alkali metal hydroxides) which can cause hydrolysis of the enol ester precursor) and those of weak bases (e.g., sodium bicarbonate) which may not function effectively in the desired rearrangement or conversion reaction of the present invention. Suitable moderate bases for use herein include the tertiary amines (e.g., triethylamine), the heterocyclic amines (e.g., pyridine) and such moderate inorganic bases as the alkali metal carbonates and phosphates (e.g., potassium carbonate and trisodium phosphate).

The reaction can be conducted in a solvent such as 1,2-dichloroethane, toluene, acetonitrile, methylene chloride, ethyl acetate, dimethylformamide, and methyl isobutyl ketone.

The following Examples further illustrate the present invention.

COMPARATIVE EXAMPLE 1

This example demonstrates the use of trimethylsilylcyanide in the preparation of 2-(2'-nitro-4'-trifluoromethylbenzoyl)-1,3-cyclohexanedione. It is presented for comparative purposes and illustrates the process described in European Published Patent Application No. 186,118.

A 250-ml flask was fitted with a condenser, addition funnel, thermometer, and magnetic stirrer. The reaction set-up was flushed with dry nitrogen, and the following reaction was carried out under a nitrogen atmosphere. The reaction flask was charged with 1,3-cyclohexanedione (8.9 gm, 0.079 mole) dissolved in alcohol-free chloroform (100 ml). This solution was cooled to below 10° C. with an ice bath. Triethylamine (24 gm, 0.24 mole) was added with stirring through the addition funnel so that the reaction temperature remained in the range of about 5° to about 10° C. The addition funnel was rinsed with a small amount of chloroform and was charged with 2-nitro-4-trifluoromethylbenzoyl chloride (20 gm, 0.079 mole). This acid chloride was added dropwise, again keeping the reaction temperature in the range of about 5° to 10° C. The reaction was allowed to stir at room temperature for 1.5 hours after the addition was completed. Trimethylsilylcyanide (0.4 gm, 0.004 mole) was added in one portion, and the reaction was allowed to stir at room temperature for 22 hours.

The color of the reaction mixture darkened during this time. The reaction mixture was cooled to below 15° C. with an ice bath and was kept at this temperature while 10% hydrochloric acid (60 ml) was added dropwise. The resulting mixture was transferred to a separatory funnel, and the lower organic phase separated and washed with water (40 ml). The organic phase was placed back in the reaction flask and cooled to below 15° C. with an ice bath. Aqueous 4% sodium hydroxide (120 ml) was added with stirring while the reaction temperature remained below 15° C.. The lower chloroform layer was separated, and the upper aqueous base layer was acidified by adding 10% hydrochloric acid (60 ml). Again, the reaction temperature was kept below 15° C. during the acidification. The resulting precipitate was collected by filtration through a sintered glass funnel. This solid product was dried in a vacuum oven at 40° C., giving 23.6 gm of the desired product. The yield was 91%.

EXAMPLE 2

This example demonstrates the use of 2-cyano-2-(trimethylsilyloxy)propane, in accordance with the present invention, in the preparation of 2-(2'-nitro-4'-trifluoromethyl)-1,3-cyclohexanedione.

The same reaction procedure and work-up employed in Example 1 were used, with the exception that 2-cyano-2-(trimethylsilyloxy)propane (0.63 gm, 0.004 mole) was used instead of the trimethylalylcyanide used in Example 1. This reaction gave 23.0 gm of product for a 89% yield.

I claim:

1. A process for converting the enol ester precursor of a benzoyl-1,3-cycloalkyldione to the benzoyl-1,3-cycloalkyldione by heating the enol ester precursor in the presence of a base and a catalytic amount of a trialkylsilylcyanohydrin having the formula

in which R is alkyl, cycloalkyl or phenyl, and R' is alkyl to effect said conversion.

2. A process as claimed in claim 1 wherein the cyclohexanedione moiety is a cyclohexyldione.

3. A process as claimed in claim 1 wherein the trialkylsilylcyanohydrin is a trimethylsilylcyanohydrin.

4. A process as claimed in claim 1 wherein a 2-(2'nitrobenzoyl)-1,3-cyclohexanedione is produced and the catalyst is a trimethylsilylcyanohydrin.

5. A process as claimed in claim 4 wherein the catalyst is 2-cyano-2-(trimethylsilyloxy)propane.

6. A process as claimed in claim 5 wherein the said catalyst is used to prepare 2-(2'-nitrobenzoyl)-5,5-dimethyl-1,3-cyclohexanedione.

7. A process as claimed in claim 5 wherein the said catalyst is used to prepare 2-(2'-nitro-4'-trifluoromethylbenzoyl)-1,3-cyclohexanedione.

8. A process as claimed in claim 5 wherein the said catalyst is used to prepare 2-(2'-nitrobenzoyl)-1,3-cyclohexanedione.

9. A process as claimed in claim 1 in which R is alkyl.

* * * * *

UNITED STATES PATENT AND TRADEMARK OFFICE
CERTIFICATE OF CORRECTION

PATENT NO. : 4,774,360

DATED : September 27, 1988

INVENTOR(S) : Elliott Bay

It is certified that error appears in the above-identified patent and that said Letters Patent is hereby corrected as shown below:

In Column 1, at line 17, the word "benzaldhyde" should read --- benzaldehyde ---.

In Column 2, at line 22, insert the word --- ester --- between the words "enol" and precursor";

at line 28, the word "arrangement" should be --- rearrangement ---.

In Claim 2, the word "cyclohexanedione" should read --- cycloalkyldione ---.

In Column 4, line 25, Claim 2, "cyclohexyldione" should read --cyclohexanedione--.

Signed and Sealed this

Twenty-seventh Day of March, 1990

Attest:

JEFFREY M. SAMUELS

*Attesting Officer*     *Acting Commissioner of Patents and Trademarks*